United States Patent [19]
Janssens

[11] Patent Number: 5,944,743
[45] Date of Patent: Aug. 31, 1999

[54] PACEMAKER SYSTEM AND METHOD WITH SPECIAL FUNCTION RATE RESPONSE

[75] Inventor: Hervé Janssens, Gent, Belgium

[73] Assignee: Vitatron Medical, B. V., Dieren, Netherlands

[21] Appl. No.: 08/858,534

[22] Filed: May 19, 1997

[51] Int. Cl.$^6$ .................................................. A61N 1/362
[52] U.S. Cl. ................................................. 607/9; 607/17
[58] Field of Search .................................. 607/9, 14, 17, 607/30, 19, 4

[56] References Cited

U.S. PATENT DOCUMENTS

| | | | |
|---|---|---|---|
| 4,884,575 | 12/1989 | Sanders | 128/419 PG |
| 4,922,930 | 5/1990 | Adkins et al. | 128/419 PG |

FOREIGN PATENT DOCUMENTS

| | | |
|---|---|---|
| 2 061 734 | 10/1980 | United Kingdom . |
| WO 95/29734 | 11/1995 | WIPO . |
| WO 97/43001 | 11/1997 | WIPO . |

OTHER PUBLICATIONS

Peters, Rene J. H., et al., "Bradycardia Dependent QT Prolongation and Ventricular Fibrillation Following Catheter Ablation of the Atrioventricular Junction With Radiofrequency Energy," Pace, vol. 17, Jun. 1994.

Jordaens, L., et al., "Sudden Death and Long–Term Survival After Ablation of the Atrioventricular Junction," Eur. J.C.P.E., 1993, vol. 3, No. 3, pp. 232–2237.

Geelen, Peter, et al., "Ventricular Fibrillation and Sudden Death After Radiofrequency Catheter Ablation of the Atrioventricular Junction," Accepted for publication in Pace 1996.

Jamie Beth Conti, et al., "Prevention of Polymorphic Ventricular Tachycardia After AV Junction Ablation," Abstracts, JACC, Feb. 1996, 376A.

*Primary Examiner*—William E. Kamm
*Assistant Examiner*—Kennedy J. Schaetzle
*Attorney, Agent, or Firm*—Michael J. Jaro; Harold Patton

[57] ABSTRACT

There is provided a pacemaker system and method for enabling special rate control for patients who have specially recognized conditions, e.g., patients who are post-ablation and thus are susceptible to bradycardia-dependent ventricular fibrillation or other arrhythmias. In a preferred embodiment, the pacemaker has a special function rate control algorithm which, for the post-ablation patient, commences pacing with a lower rate limit at a high start value of around 80–100 bpm, and decays the lower rate limit down to an end value of about 60–70 bpm over a duration of about a month. Additionally, the pacemaker is provided with one or more selectable special function rate response algorithms, for enabling higher rate response to patient exercise and demand for increase cardiac output. The combination of the gradual decay of lower rate limit over the programmable duration as well as the specially programmable rate response enables optimization of pacing so as to prevent arrhythmias.

21 Claims, 4 Drawing Sheets

PACEMAKER SYSTEM AND METHOD WITH SPECIAL FUNCTION RATE RESPONSE

FIELD OF THE INVENTION

This invention relates to cardiac pacemakers and, more particularly, implantable cardiac pacemakers with programmable rate control.

BACKGROUND OF THE INVENTION

Pacemaker systems with rate control have become widely used in the art. Rate control may be provided by employing one or more rate responsive sensors, e.g., sensors which determine a parameter such as Q-T interval, exercise, etc., from which the desired pacing rate to match the patient's cardiac's demand can be determined. Such rate responsive pacemakers contain algorithms for converting the sensed parameters into pacing rate, e.g., increased activity results in a higher pacing rate. Further, it is known to program certain data relating to pacing rate from an external programmer, e.g., the values of lower rate limit (LRL) and upper rate limit (URL) can be programmed in this manner.

It has been determined that under special circumstances, it is desired to control pacing rate of an implanted pacemaker in accordance with a special function, i.e., at a rate or rates which would not otherwise be indicated. For example, it has been determined that following radio frequency catheter ablation of the atrioventricular junction, there is a certain incidence of ventricular fibrillation or sudden death. See, for example, the article of Peters et al., "Bradycardia Dependent QT Prolongation and Ventricular Fibrillation Following Catheter Ablation of the Atrioventricular Junction With Radiofrequency Energy," PACE, Vol. 17, January 1994; Jordaens et al., "Sudden Death and Long-Term Survival After Ablation of the Atrioventricular Junction," EUR.J.C.P.E., Vol. 3, Nov. 3, 1993; and Geelen et al., "Ventricular Fibrillation and Sudden Death After Radiofrequency Catheter Ablation of the Atrioventricular Junction," PACE, 1996. Indeed, it has been determined that for pacemaker patients with an LRL in the area of 60 bpm, post-ablation there is a risk of about 6% that the patient will develop bradycardia-dependent ventricular fibrillation. In such post-ablation circumstances, the patient's natural fast ventricular rate is replaced by the pacemaker rate. While lower rate pacing does not remove the danger, episodes of ventricular extra-systole (VES) and ventricular tachycardia can be suppressed by overdrive pacing at a higher rate, e.g., 80–90 bpm, or greater. Accordingly, it is known to program a lower rate limit to such a relatively high rate of about 90 bpm, and to then reprogram the lower rate limit back to a more normal rate, e.g., 60 bpm, following a month or so.

However, there remain certain problems with this post-ablation technique. First, the patient comfort may be sacrificed by maintaining the lower rate limit at the constant high rate for too long a period of time. Further, the patient then needs to be re-programmed by the physician, at which time LRL is abruptly dropped to a lower value, e.g., 60 bpm. Further, this procedure provides no flexibility, and does not account for the fact that the high rate overdrive need is not constant, but can be adjusted downward over a time period of approximately a month. Further, the prior art does not take into account the effects of patient exercise. Since the patient remains vulnerable to bradycardia-dependent fibrillation, the rate response during exercise should be adjusted to be more appropriate to this particular situation.

Accordingly, there is a need for a pacemaker system and method for providing special function rate control, to be used for situations such as a post-ablation period or other special diagnosed circumstances where normal rate control is unsatisfactory.

SUMMARY OF THE INVENTION

It is an object of this invention to provide an implantable pacemaker system and method for carrying out special function rate control for dealing with situations such as faced by patients following catheter ablation of the atrioventricular junction. Specifically, the object is to provide a pacemaker which can be enabled to switch into a specialized rate control routine for varying minimum pacing rate, as well as varying the rate response during periods of patient exercise. For the special function of dealing with a post-ablation period, the pacemaker system of this invention provides for an initial high low rate limit, e.g., 80–110 ppm followed by a gradual decay of LRL over a predetermined period such as one month.

The special function rate feature of this invention can be enabled by external programming directly after the event or determination that requires the special function, e.g., following an ablation procedure. In a preferred embodiment, the escape interval is initially set to a value corresponding to a high LRL of at least 80 bpm (or ppm—pulse per minute), which escape interval increases in accordance with a pre-determined decay function over a given time duration to a value corresponding to a normal lower rate limit. As a specific example, the system can be enabled to start at a rate corresponding to about 93.75 bpm, which rate is then decremented every two hours by incrementing the escape interval 1 ms, whereby after 30 days the rate is down to 60 bpm.

For a preferred embodiment of a rate responsive pacemaker, the pacemaker stores a normal rate response (RR) algorithm for correlating a sensed parameter into pacing rate, as well as one or more selectable special function algorithms. When the special function rate control of this invention is enabled, the selected rate response function is more aggressive, i.e., it reacts more aggressively to exercise so as to take pacing rate more quickly toward the upper rate limit after the onset of exercise.

DETAILED DESCRIPTION OF THE PREFERRED EMBODIMENTS

Figure 1:
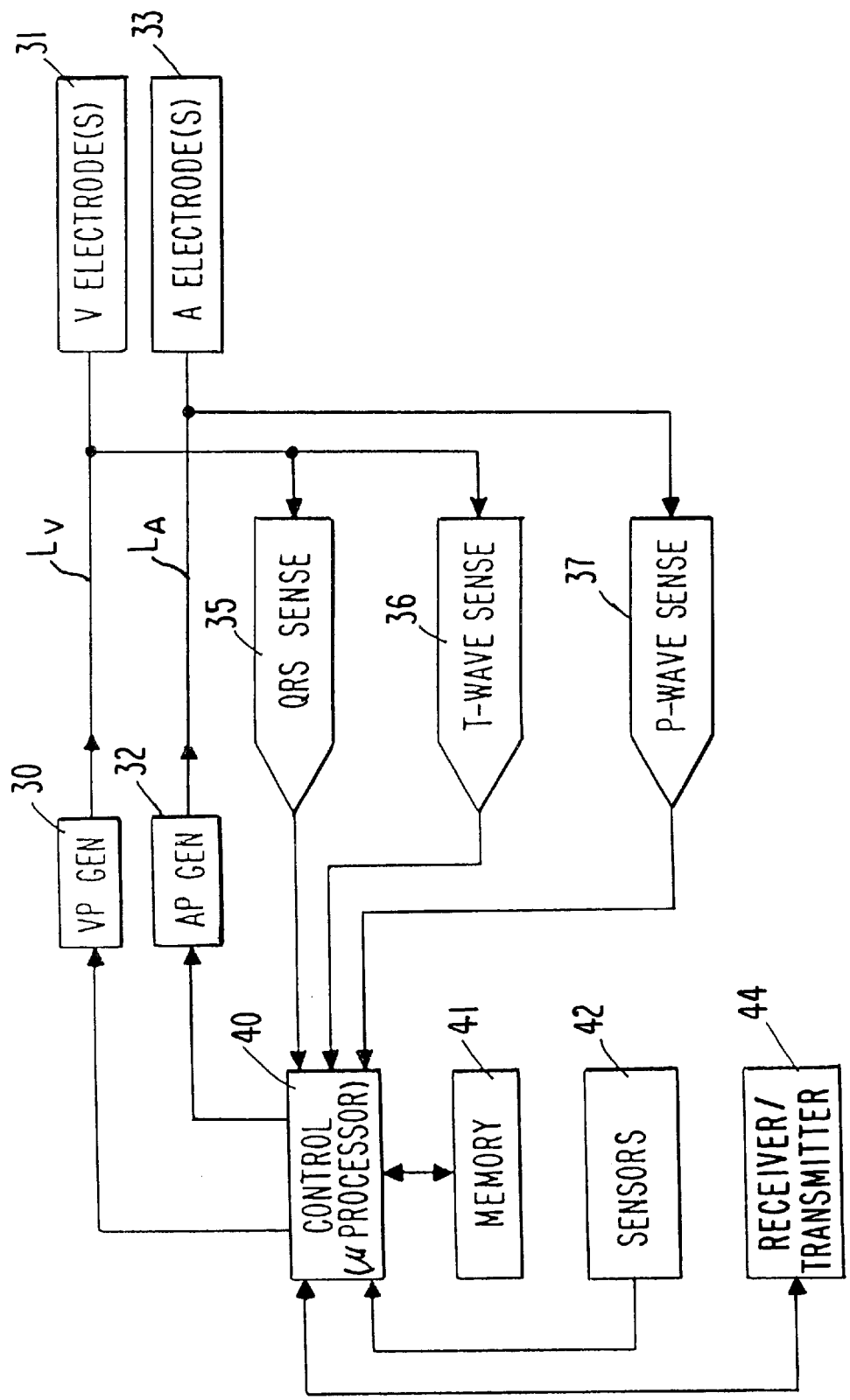
FIG. 1 is a block diagram of the primary components of a pacemaker in accordance with this invention.

Referring now to FIG. 1, there is shown a block diagram of an illustrative pacemaker system for use in the practice of this invention. The block diagram of FIG. 1 shows the primary functional components of a pacemaker, which components and their interconnections are well known in the pacemaker art. A VP generator 30 produces ventricular pace pulses under control of control block 40. The output of generator 30 is connected through a pacing lead $L_v$ to a ventricular electrode or electrodes indicated at 31, for pacing of the patient's ventricle. The electrode or electrodes 31 also sense signals in the patient's ventricle, natural and evoked. Signals sensed at electrodes 31 are connected to a QRS sense amplifier circuit 35, as well as to a T-wave sense amplifier 36. By a technique well known in the art, amplifier 35 is enabled for a window corresponding to the expected arrival of the QRS, under control of circuit 40; similarly the T-wave amplifier is enabled for a window of time around the expected T-wave, likewise under the control of circuit 40. Thus, ventricular senses (VS) and T-waves are detected and inputted into control 40, for use by the pacemaker. For a dual chamber pacemaker, there is also an atrial pulse generator 32, which delivers atrial pace pulses under control of control circuit 40. These pulses are connected through an atrial lead $L_A$ to atrial electrode or electrodes designated at 33. Natural P-waves, or evoked atrial responses, are sensed by the atrial electrodes 33, and connected to P-wave sense amplifier 37, the output of which is connected back to control block 40.

Control block 40 performs the various logic and processing functions of a modern pacemaker, and suitably comprises a microprocessor. The microprocessor circuit itself contains some memory, and there may be additional memory, RAM/ROM, as indicated at block 41. The allocation of hardware and software to the structure and control block 40 is a matter of design choice, and not important to the scope of this invention. Also shown are one or more sensors 42, for determining one or more parameters from which rate responsive control can be achieved, again in a known fashion. Additionally, the stimulus-T, or Q-T interval can be derived and used as the RR parameter, in a known manner. Block 44 illustrates a receiver-transmitter for communicating with an external programmer by telemetry, in a known fashion. Thus, program instructions from an external transmitter are received at 44 and coupled into control block 40; likewise data collected by the pacemaker concerning pacemaker operating variables and/or diagnostic data may be downloaded through unit 44 to the external programmer, in a known manner.

In the practice of this invention, an external command for putting the pacemaker into a special function rate control mode is received at receiver-transmitter 44, and conveyed to the control unit 40. The normal rate response algorithm, and the selectable special function response algorithm, are stored in memory 41, and selected in response to a programmed signal. It is to be understood that while a decay response appropriate for a post-ablation patient is presented as the preferred embodiment, any other special function program may be stored and enabled upon appropriate command.

Figure 2:
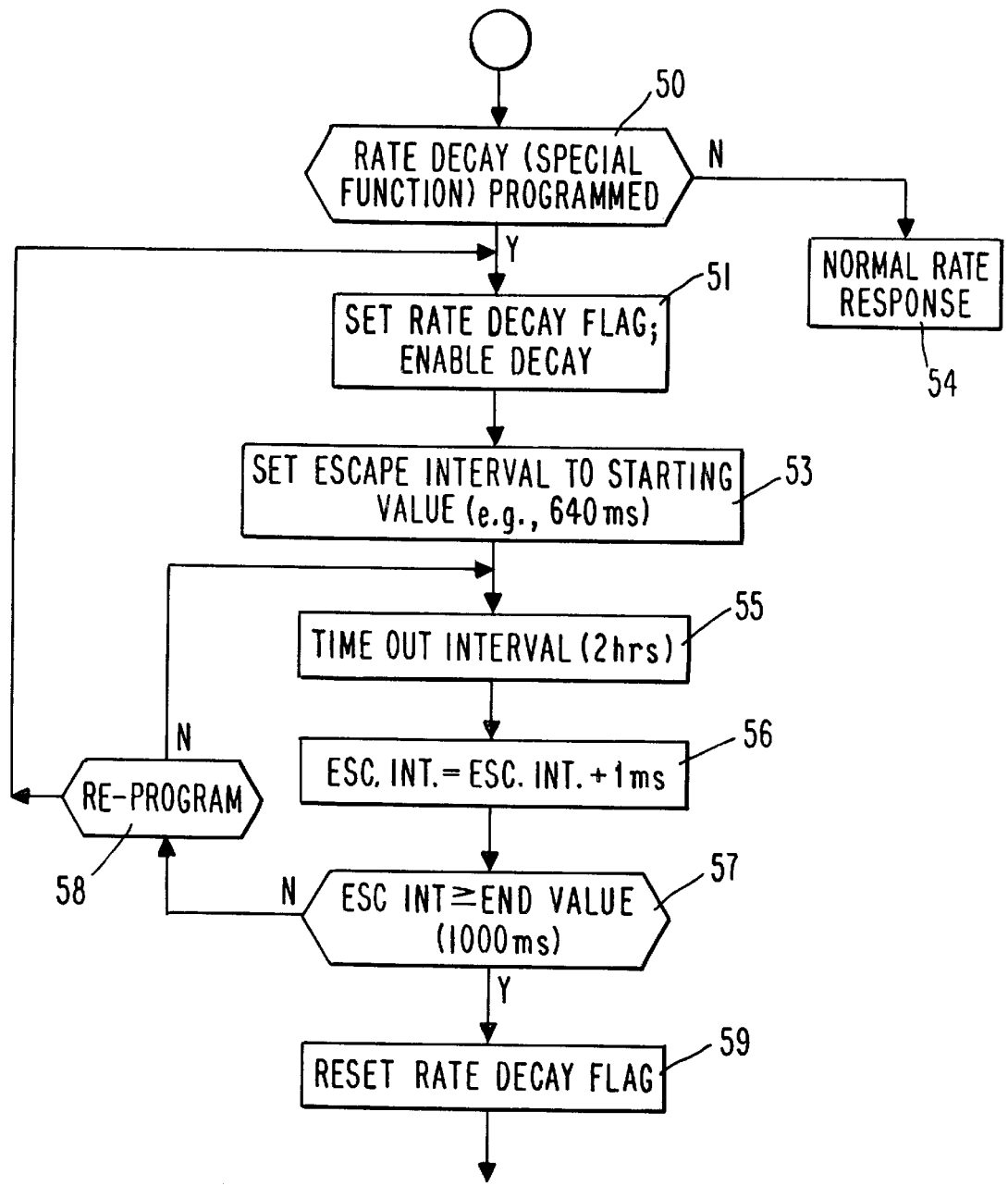
FIG. 2 is a flow diagram showing the primary steps taken in a rate responsive pacemaker in accordance with this invention, including the steps of enabling the pacemaker to go into special function rate control.

Referring now to FIG. 2, there is shown a flow diagram of the primary steps taken in controlling rate in accordance with this invention. The steps preferably carried out under software control. It is to be understood that the pacemaker is programmed with normal values for LRL and URL, as well as a normal rate response correlation function for correlating a sensed parameter such as activity with a rate response rate. At block 50, the pacemaker determines whether a rate decay, or special rate function is programmed. If no, the pacemaker utilizes the normal rate response algorithm, whatever that may be, as indicated at block 54. However, if a special function is programmed, the pacemaker sets the decay flag, or special function flag as indicated at block 51, which enables the special function routine. When this flag is set, the pacemaker sets the escape interval to a starting value, e.g., 640 ms, as indicated at 53. Six hundred forty ms corresponds to a starting rate of 93.75 bpm. As stated above, the start value for pacing rate during the duration of special rate function pacing is to be high enough to override ventricular fibrillation. The starting rate may be set by the physician, and may suitably be in the range of 80–110 bpm, or higher. The indicated starting rate of 93.75 is exemplary, and corresponds to a linear decay over one month down to an end value of 60 bpm.

Still referring to FIG. 2, at step 55 the pacemaker times out an interval, e.g., 2 hours. Upon timeout of this interval, as indicated at 56 the escape interval is incremented by 1 ms. Following this, it is determined whether the escape interval is equal to or greater than the end value, an exemplary end value being 1,000 ms which corresponds to 60 bpm. If no, the routine branches to block 58, and determines whether the special function is to be reprogrammed. If no, the routine goes back to 55, and commences timeout of the next 2-hour interval. If yes, the routine goes back to 51 and again enables the special decay function, which at this point may be a reprogrammed function. Reprogramming may consist simply of starting a new decay routine, changing the time duration, changing the start rate or the end rate, or any combination of these special function variables.

In the absence of reprogramming, the routine of FIG. 2 continually re-loops, timing out 2-hour intervals, following each interval with an increase of the escape interval by 1 ms. In this manner, after 30 days, the escape interval is incremented to 1,000 ms, corresponding to 60 bpm. While this linear decay is illustrated as exemplary, it is to be understood that any other desired decay function can be utilized in accordance with this invention. After the pacing rate has increased to the end value, at block 59 the rate decay flag is reset, such that the pacemaker then goes to a normal rate response mode.

Figure 3:
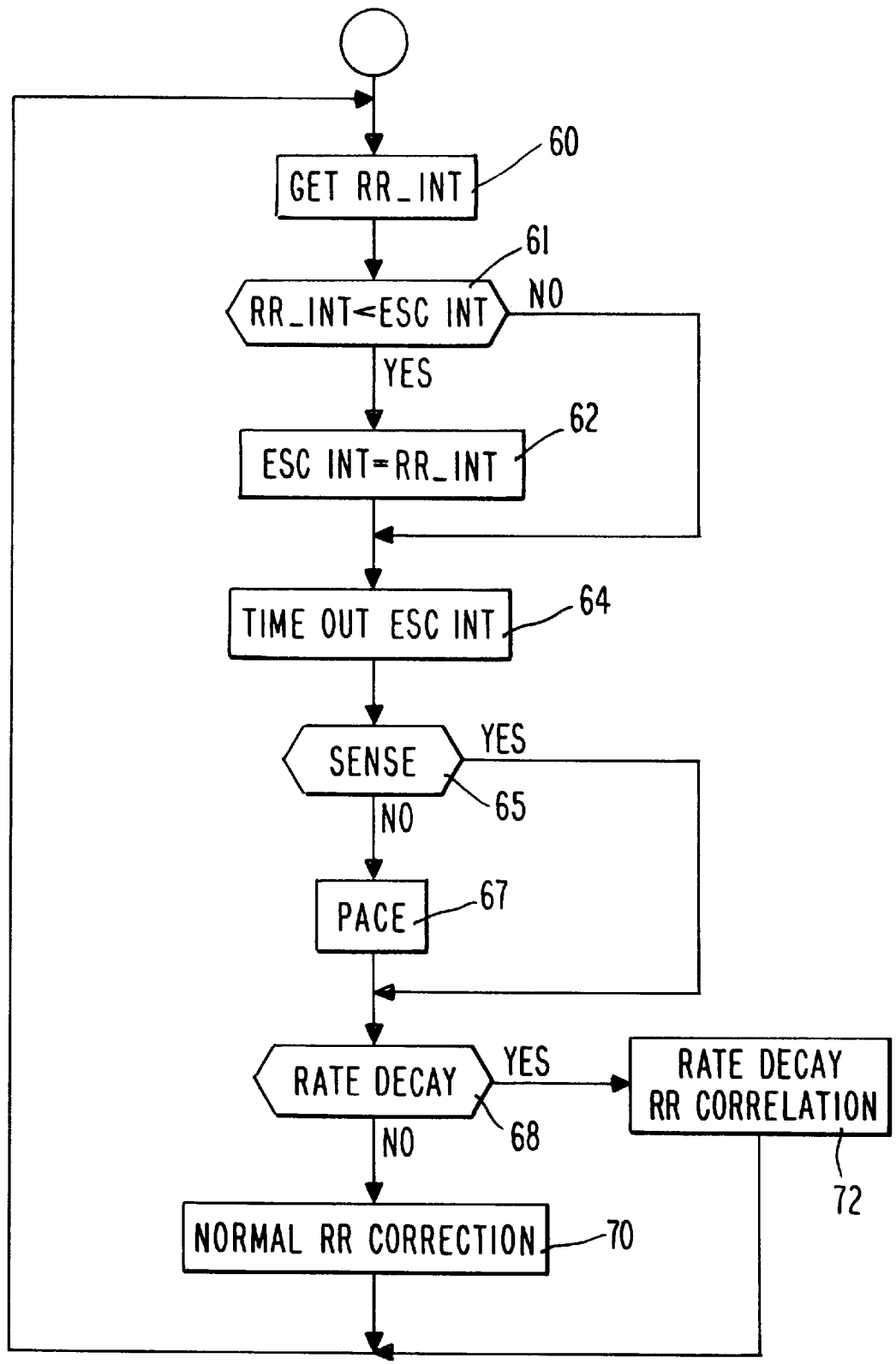
FIG. 3 is a flow diagram illustrating rate responsive override of the pacing rate in accordance with this invention.

Referring now to FIG. 3, there is shown a flow diagram illustrating the inclusion of rate response as derived from one or more rate-indicating sensors. This flow diagram shows steps which are taken every pacemaker cycle during the duration of this special function. At 60, the pacemaker gets the rate response escape interval, indicated as RR_int. Then, at 61, RR_int is compared to the escape interval, the escape interval being set by the special function, or decay routine as seen at block 56 of FIG. 2. If RR_int is not less than the escape interval, the routine skips to block 64. However, if this comparison indicates that the RR_int is less than the escape interval, then at 62 the escape interval is set equal to RR_int. At 64, the escape interval is timed out. At 65, it is determined whether there has been a sense. If yes, then pacing is inhibited in the normal fashion. If no, then a pace pulse is delivered as indicated at 67. Then, at 68, it is determined whether the pacemaker remains in the rate decay or special function mode. If yes, at 72 the rate decay RR correlation is enabled; if no, then at 70 the normal RR correlation is enabled.

Figure 4A:
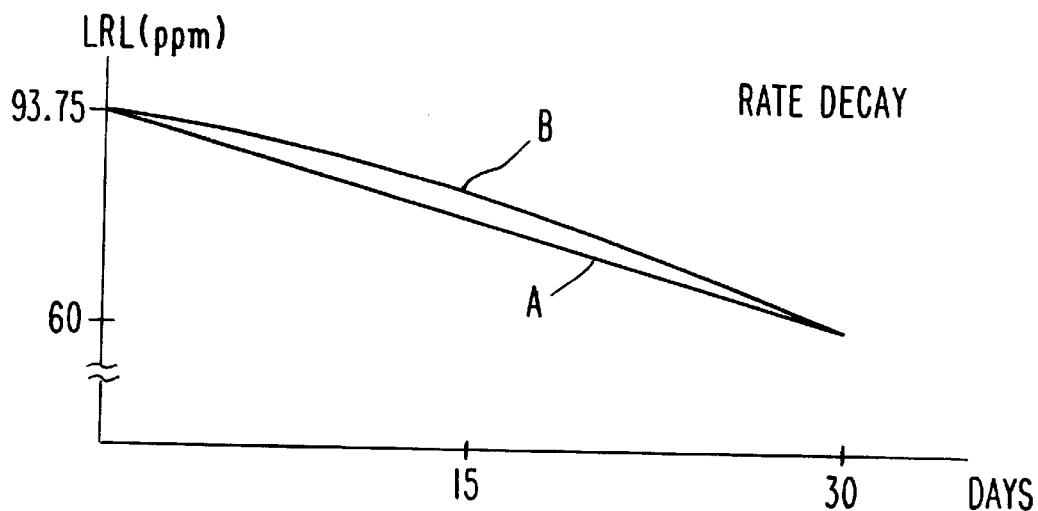
FIG. 4a is a diagram illustrating a linear and a curvilinear decay function in accordance with this invention.

Referring to FIG. 4a, there is shown a pair of curves indicating linear and non-linear versions of a decay function. The straight line indicated at A indicates a linear decrease in pacing rate from 93.75 down to 60 bpm, over 30 days, as described above. The curve at B shows a non-linear change, wherein higher pacing rates are maintained for a longer time, as compared to the curve at A. The exact function can, of course, be determined as a matter of choice, suitably matching the physician's experience with such cases. Note that if the decay function is reprogrammed at any time, the doctor can select a plurality of different responses stored in memory. Of course, for other patient conditions requiring different pacing strategies, the response is formulated to carry out the prescribed strategy.

Figure 4B:
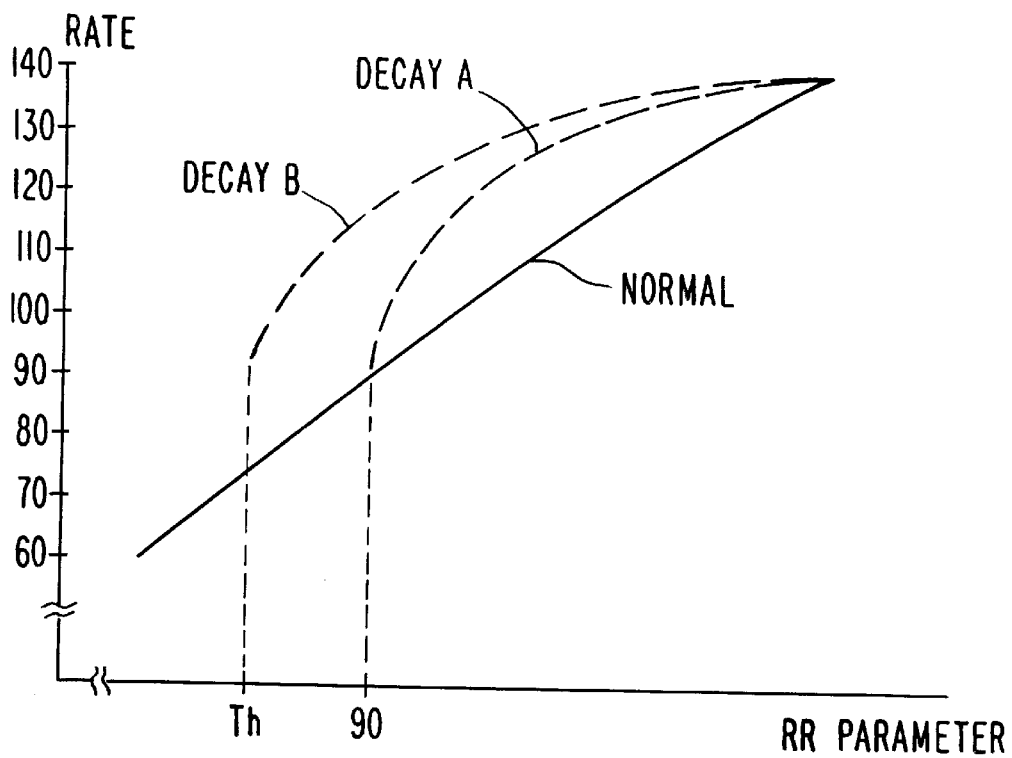
FIG. 4b is a diagram illustrating a more aggressive rate response in accordance with this invention.

Referring to FIG. 4b, there are shown several different forms of rate response overdrive. The straight line shows a normal rate response correlation function, where increases in the rate response parameter (e.g., activity) correspond to linear increases in rate. As indicated, the rate increases linearly from 60 to 140 bpm, as a function of the rate response parameter. By contrast, the dashed line indicated as "decay A" shows a more aggressive correlation function, which kicks in at 90 bpm. Thus, for this rate response, and assuming the decay rate is 90 bpm, when the rate response parameter indicates a pacing rate greater than 90 it is more aggressive in being incremented toward the upper rate limit. This response may be tied to the decay rate, i.e., if the decay rate is down to 80 bpm from a higher starting point, then the more aggressive rate response function takes over anytime a rate greater than a rate of 80 is indicated. The curve marked "decay B" is a variation, wherein once the rate response parameter rises above a predetermined threshold (Th), the rate indicated by the RR parameter jumps incrementally, e.g., to 90 bpm, and then curves up toward the upper rate limit. These curves are examples, and are intended to illustrate that the precise nature of the special function rate response correlation is something that can be programmed to take into account patient history or any other known facts.

It is to be understood that the special RR function can be implemented without the decay function. Thus, a patient condition may not present a need for a special LRL, but may suggest a special rate response to exercise or other conditions. In this case, the decay program is bypassed, but the special function RR correlation is enabled for a predetermined duration, or until reprogramming by the physician.

I claim:

1. An implantable pacing system adapted for special function rate control, comprising:

pulse generator means for generating and delivering pacing pulses to a patient;

rate control means for controlling the rate of generated pacing pulses, said rate control means having special function means for controlling said pulse generator means to pace at rates in accordance with a special function, said special function means having high rate means for setting an escape interval corresponding to a high rate of at least 80 ppm; means for timing out a time duration having a length in the range of 15–35 days; and decay means for increasing said escape interval with a predetermined decay function over a predetermined time duration to a value corresponding to a predetermined lower rate limit, and enabling means for enabling said special function means.

2. The system as described in claim 1, wherein said decay means has means for incrementing said escape interval regularly.

3. The system as described in claim 2, wherein said incrementing means has means for incrementing said escape interval about 1 ms every 2 hours.

4. The system as described in claim 1, wherein said high rate means sets an escape interval corresponding to a rate in the range of 90–110 ppm.

5. An implantable pacing system adapted for special function rate control, comprising:

pulse generator means for generating and delivering pacing pulses to a patient;

rate control means for controlling the rate of generated pacing pulses, said rate control means having special function means for controlling said pulse generator means to pace at rates in accordance with a special function, said special function means having high rate means for setting an escape interval corresponding to a high rate of at least 80 ppm:

decay means for increasing said escape interval with a predetermined decay function over a predetermined time duration to a value corresponding to a predetermined lower rate limit, and enabling means for enabling said special function means: and programmable repeat means for controlling said high rate means to reset the escape interval to another rate.

6. The system as described in claim 5, comprising programmable change means for changing said decay function.

7. The system as described in claim 6, comprising rate control means for determining a desired pacing rate as a function of at least one measured patient parameter, and means for setting the pacing rate of generated pace pulses in accordance with said determined rate when said determined rate is greater than the rate set by said decay means.

8. The system as described in claim 7, wherein said rate control means has an aggressive function and a normal function, and means for enabling said aggressive function when said special function means is enabled.

9. A rate responsive implantable cardiac pacing system, comprising:

pulse generator means for generating and delivering pacing pulses to a patient's heart;

special function means for determining a special function rate corresponding to a predetermined special function, said special function comprising starting at a rate of at least 80 ppm and decaying to an end rate below 70 ppm within a predetermined time duration;

enabling means for enabling operation of said special function means;

rate responsive means for determining a rate responsive pacing rate as a function of at least one patient parameter; and rate control means for controlling the rate of pacing pulses generated by said generator means to be the greater of said rate responsive rate and said special function rate.

10. The system as described in claim 9, wherein said rate responsive means comprises normal means for determining said responsive rate in accordance with a first algorithm to be used normally, and aggressive means for determining said responsive rate in accordance with a second more aggressive algorithm, and second enabling means for enabling said aggressive means to determine the responsive rate when said special function means is enabled.

11. The system as described in claim 10, wherein said aggressive means algorithm raises pacing rate rapidly in response to exercise that calls for a pacing rate above said special function rate.

12. The system as described in claim 9, wherein said special function rate starts at a rate at least 90 ppm, and decays to a rate of 70 ppm or lower over a time of about 30 days.

13. The system as described in claim 9, wherein said enabling means comprises programmable means for receiving a program signal from an external source.

14. The system as described in claim 13, wherein said programmable means further comprises means for receiving data for determining said starting rate, said end rate, and said duration.

15. A method of pacing with an implanted pacemaker system, comprising:

setting a lower rate limit at a start value in a range of 80–110 ppm;

timing out a decay period of at least two weeks;

adjusting said lower rate limit downward from said start limit to an end limit over said decay period; and pacing at at least said lower rate limit as said limit is adjusted during said decay period.

16. The method as described in claim 15, comprising programming said lower rate limit, said decay period, and said end limit into said implanted pacemaker system.

17. The method as described in claim 15, comprising obtaining a measure of patient cardiac demand and determining a demand responsive rate as a function of said demand, and pacing at said demand responsive rate when said demand responsive rate is higher than said adjusted lower rate limit.

18. The method as described in claim 17, comprising pacing at a rate greater than said demand responsive rate when said demand responsive rate is greater than said adjusted limit, and said decay period is being timed out.

19. The method as described in claim 15, comprising adjusting said lower rate limit downward by a fixed increment every predetermined interval of time.

20. An implantable rate responsive pacing system with special function rate control, comprising:

pulse means for generating and delivering pacing pulses to a patient's heart;

a stored special function routine for determining a first pacing rate which is variable as a function of time;

parameter means for sensing at least one patient parameter indicative of desired pacing rate;

a stored parameter routine for determining a second pacing rate which is a function of said at least one patient parameter; and rate control means for controlling the rate of said pacing pulses as a function of said first and second determined pacing rates and in accordance with the highest of said first and second determined pacing rates.

21. The system as described in claim 20, wherein said rate control means comprises LRL means for limiting the lower rate of said pacing rate to said first pacing rate.

* * * * *